United States Patent [19]

Buchanan

[11] 4,203,971
[45] May 20, 1980

[54] *NEISSERIA GONORRHOEAE* VACCINE

[75] Inventor: Thomas M. Buchanan, Seattle, Wash.

[73] Assignee: Government of the United States, Washington, D.C.

[21] Appl. No.: 889,343

[22] Filed: Mar. 23, 1978

[51] Int. Cl.$^2$ ............................................. A61K 39/02
[52] U.S. Cl. ...................................................... 424/92
[58] Field of Search .......................................... 424/92

[56] References Cited

U.S. PATENT DOCUMENTS

| | | | |
|---|---|---|---|
| 1,409,796 | 3/1922 | Thomson | 424/92 |
| 1,717,198 | 6/1929 | Ferry | 424/92 |
| 2,156,240 | 4/1939 | Hibbert | 424/92 |
| 2,513,327 | 7/1950 | Ichelson | 424/92 |
| 3,567,822 | 3/1971 | Sarbach et al. | 424/92 |
| 3,577,527 | 5/1971 | Edwards | 424/92 |
| 4,029,756 | 6/1977 | Gaafar | 424/1 |
| 4,066,744 | 1/1978 | Price et al. | 424/12 |

OTHER PUBLICATIONS

Robbins, J. B. Br. J. Vener. Dis. 53(3):170–172, Jun. 1977, "Problems Posed by Potential Gonococcal Vaccines Viewed from the Vantage Point of a Control Agency".
Ovchinnikov, N. M. et al., Vestn Dermatol Venerol (12):28–32, Dec. 1976 (Russ.) "Protective Properties of Gonococcal Vaccines".
Buchanan, T. M. et al., J. Infect. Dis. 135(6):879–887, Jun. 1977, "Immunity to Gonococcal Infection Induced by Vaccination with Isolated Outer Membranes of *Neisseria gonorrhoeae* in Guinea Pigs".
Buchanan, T. M. et al., J. Infect. Dis. 136 Suppl: S132–137, Aug. 1977, "Protection Against Infection with *Neisseria gonorrhoeae* by Immunization with Outer Membrane Protein Complex and Purified Pili".
Buchanan et al., Clinical Research 26(3):391A(1978) Human Immune Response to Principal Outer Membrane Protein (POMP) During Disseminated Gonococcal Infection (DGI).
Buchanan et al., Immunobiol. *Neisseria gonorrhoeae* Proc. Conf. (1978):145–154, p. 14, and Principal Outer Membrane Protein of *Neisseria gonorrhoeae*: Immunochemical Structural and Pathogenic Aspects, in Chem. Abstr. 89 #2133309 (1978).
Johnston Immunobiol. *Neisseria gonorrhoeae* Proc. Conf. (1978):121–129 Antigenic Profile of an Outer Membrane Complex of *Neisseria gonorrhoeae*, Responsible for Serotype Specificity, in Chem. Abstr. 89 #213420m (1978).
Robbins, John B., Immunobiol. *Neisseria gonorrhoeae* Proc. Conf. (1978):391–394, "Disease Control for Gonorrhea by Vaccine Immunoprophylaxis:The Next Step?", Conf. 18–20, Jan. 1978, American Society for Microbiology, Wash. D.C. Sep. 29, 1978.

*Primary Examiner*—Shep K. Rose
*Attorney, Agent, or Firm*—Holman & Stern

[57] ABSTRACT

A vaccine affording protection against infection by *Neisseria gonorrhoeae* (N.g.) microorganisms is prepared from principal outer protein material isolated from gonococci.

2 Claims, 1 Drawing Figure

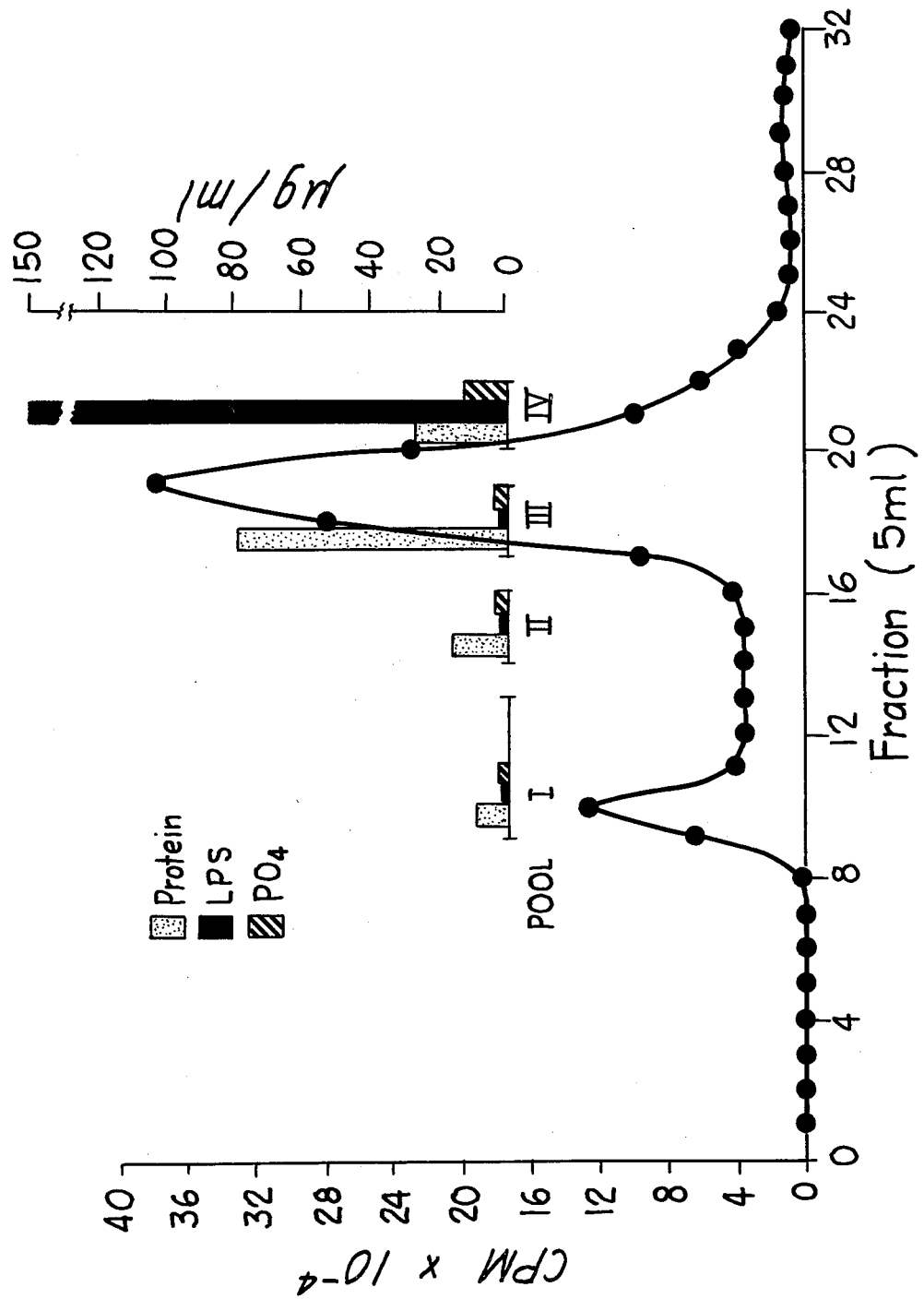

NEISSERIA GONORRHOEAE VACCINE

BACKGROUND OF THE INVENTION

Gonorrhoeae is a most persistant pandemic affliction of the human race. In the United States alone, approximately 4 million persons annually appear in clinics and physicians offices with this sexually transmitted disease. These individuals, so experience has shown, form a hard core source of new infections for additional individuals, and are, themselves, consistently becoming reinfected. There is a significant and growing need for a vaccine to contain this contagion.

Despite this urgent demand, no successful vaccine has yet become available. One of the principal problems which has impeded the production of a vaccine is the antigenic heterogeneity of the N.g. microorganisms. Another is the complex nature of the microorganisms. It has been repeatedly observed that the N.g. strain responsible for an epidemic in one community has a substantially different antigenic profile from the strain which is the source of infection in another community. As a result, the development of a vaccine effective against the former strain will not guarantee success against the latter strain. The problem then becomes one of discovering and isolating an antigen which is common to all strains and capable of eliciting an antibody response at a level which will afford protection against infection or reinfection. Alternatively, the problem could be dealt with by the discovery and isolation of an antigen which, while not necessarily common to all N.g. microorganisms, is capable of eliciting a protective antibody response against all of them. A more realistic and practical goal would be to discover and isolate a small number of antigens which could be combined in one vaccine to stimulate immunity from infection from most, if not all, N.g. microorganisms.

As indicated above, the problem of isolating useful antigens is further complicated by the complexity of the cellular structure of the N.g. microorganisms. Antigens are present in the pili, principal outer membrane, and lipopolysaccharides (LPS) in the cell. To separate these antigens in a useful form, free of contamination by other materials and by each other, is indeed a challenge. Moreover, some of the contaminants are toxic. LPS contaminants in isolates which might be considered potentially useful for vaccines have been observed to cause fever, shock and death in experimental animals. In humans, they would be expected to cause severe pain and swelling at the site of infection, severely elevated temperature, chills and perspiration.

Since antigens are proteins, it is necessary to utilize an isolation procedure which does not denature and thereby inactivate the protein. Moreover, it is necessary that the antigen isolated be immunogenic. To be useful as a vaccine, it is not sufficient that the antigen merely conjugate with existing antibodies. It must stimulate the host to produce a strong and persistant antibody response.

THE INVENTION

It has now been discovered that by a very specific treatment to be described more fully hereinafter it is possible to isolate from whole gonococci a principal outer membrane antigen which is bactericidal but not opsonic, is substantially free of other protein, and contains no toxic quantities of LPS. This antigen has been designated POMP antigen. The antigens isolated from different strains vary slightly amongst each other, but have many features in common. Not all stimulate a high antibody response which protects against all strains of gonococci. However, so far as has been observed, each of them generate a sufficiently high antibody response to protect against infections caused by any of a large number of strains. Thus, a multivalent vaccine containing, for example, 5 to 8 POMP antigens will afford broad protection against infection by a large number of different N.g. strains.

The POMP antigens of this invention are bactericidal but not opsonic. That is they stimulate the production of bactericidal antibodies which kill invading gonococci. This is in contrast to opsonic antibodies which function by rendering bacteria or other invading cells susceptible to phagocytosis. So far as is known, the POMP antigens of this invention are the first POMP isolates from gonococci which are bactericidal but not opsonic.

In addition to their common property of stimulating the production of bactericidal antibodies, the POMP antigens of the invention are also characterized by molecular weight subunits of from about 34,000 to 39,000 Daltons. They contain both hydrophobic and hydrophilic groups. The carbohydrate content is about 4%, and their protein content at least about 96% by weight. As previously indicated, they vary somewhat in antigenic profile. They also have slightly different subunit molecular weights, although all are in the range of from 34,000 to 39,000 Daltons.

There have been many previous attempts to separate POMP antigens without causing denaturation and with retention of immunogenicity. These attempts have included, for example, column chromatography over various absorbents in differing buffer compositions, separations based on surfactants, or clathrate compounds such as urea, procedures based on charge differences such as DEAE chromatography, isoelectric focusing, Pevikon block electrophoresis, and procedures based on density differences, including ultracentrifugation in sucrose or cesium chloride gradients. None, so far as is known, have been successful.

In accordance with the procedure of this invention, the gonococci are grown for 20 hours on solid g.c. agar base media containing 1% defined supplement [White, L. A. and Kellog, D. S.; Appl. Microbiol. 13:171 (1965)], at 36.5° C. in the presence of 3% $CO_2$. The organisms are suspended in ice cold 0.15 M sodium chloride and centrifuged at 12,000×g for 10 minutes. The organism pellet is placed into 100 ml glass bottles in a ratio of 2 g wet weight or organisms to 25 cc of lithium acetate, 10 mM NaEDTA pH 5.9 buffer, and glass beads are added to adjust the final volume to 50 ml. These tightly capped bottles are placed in a water bath gyratory shaker, and shaken for 2 hours at 45° C. at 200 rpm according to the method of Johnston et al, J. Exp, Med. 143, 741 (1976). The liquid suspension is removed with a Pasteur pipette and centrifuged at 12,000×g for 10 minutes. The supernate is centrifuged at 30,000×g for 40 minutes. The supernate from this treatment is spun at 130,000×g for one hour, and the clear glassy pellet retained. A portion of the pellet is labelled with $^{125}$I by the chloramine procedure of Greenwood et al, Biochem. J. 89, 114 (1963). The pellet is resuspended in a buffer containing 50 mM glycine pH 9.0, 5 mM EDTA and 1.5% sodium deoxycholate and applied along with 100 μl of labelled pellet material to a 1.5×90 cm Sepharose 6B column (Pharmacia, Piscataway, N.J.) and chromatographed in the same buffer. Five ml fractions are collected and assessed for radioactivity, total phosphate, LPS and protein concentrations. Total LPS content is estimated by 2-keto-3-deoxy-octulosonic (KDO) determination using commercially available purified Escherichia coli 055:B5 LPS (Difco Labs, Detroit, Mich.) as a standard according to the method of Osborne, Proc. Nat'l Acad. Sci, U.S.A. 50, 499 (1963). Protein is determined by the method of Lowry et al, J. Biol. Chem. 193, 265 (1951). Phosphate is determined by the method of Ames and Dubin, J. Biol, Chem. 235, 769 (1960). POMP purity is assayed by sodium dodecyl sulphate polyacrylamide gel electrophoresis in discs or slabs after the method of Weber and Osborn, J. Biol. Chem. 244,4406 (1969) and Maizel, Methods. Vivol. 5, 179 (1971).

The results are shown in the FIGURE which illustrates the typical chromatography pattern of gonococcal outer membrane 130,000×g pellets (with a tracer of $^{25}$I-labelled pellet) run over Sepharose 6B in the presence of deoxycholate buffer. The fractions of the first peak are utilized for the preparation of a vaccine. Sepharose 6B is a linear polysaccharide consisting of alternate residues of D-galactose and 3,6-anhydro-L-galactose. Its exclusion limit is 4,000,000. Thus the void volume constituents initially have a molecular weight of at least 4,000,000. Materials with lesser molecular weight are initially retained on the column, although with sufficient washing, they can be released.

Typically, for the preparation of a vaccine combined fractions 9 through 12 will be mixed with 95% ethanol at a ratio of 5.33 ml of ethanol for each ml of the combined fractions to form an 80% ethanol mix. The mixture is centrifuged, and the pellet resuspended in 95% ethanol and again centrifuged. The pellet is taken up in 5 mM glycine-sodium hydroxide, pH 9, and the concentration adjusted to 100–200 micrograms per ml. The mix is filter sterilized through a 0.22 micron millipore filter and to it is added 0.1 volume of filter sterilized 1.0 M phosphate buffer, pH 7.4, containing 1:1000 thimerosal, to produce a product containing vaccine protein, 100 millimolar phosphate buffer, thimerosal at 1:10,000, and a final pH of 7.4.

There is thus prepared a vaccine for human use containing 100 to 150 microgramps per ml. of protein. An immunizing dose of this vaccine will normally be 0.5 cc administered subcutaneously.

For the preparation of a multivalent vaccine containing POMP antigen from several strains, the initial concentration of pellet in the glycine-sodium hydroxide for each isolate will be adjusted. For example, for a pentavalent vaccine, the initial concentration of each pellet will be 500 to 1000 micrograms per ml instead of 100 to 200. The volumes of the other materials will be adjusted accordingly so that the final product is five times more concentrated. Five separate products will then be mixed. The immunizing dose for the multivalent vaccine will be the same as for the univalent material.

As indicated, a useful vaccine within the scope of the invention will normally contain at least one POMP antigen at a concentration of from about 100 to 500 micrograms per ml. With multivalent vaccines, each of the POMP materials will be presented at approximately the same concentration. A useful unit dose will normally be 0.5 cc. However, other dosage forms may be prepared suitable for injection to contain from 0.2 to 0.7 cc. It may be desirable in certain instances to provide for booster treatment, that is administration of one dosage unit at a particular level, say 0.5 cc, followed after a selected period of time with another administration of the same or a different dosage unit, to enhance the human immune response to the vaccine.

What is claimed is:

1. A vaccine for protecting humans against infection by Neisseria gonorrhoeae microorganisms containing at least one POMP antigen free of contaminants which are toxic to humans characterized by the ability to elicit a bactericidal response in humans, consisting essentially of subunits with molecular weights of from 34,000 to 39,000 Daltons, containing both hydrophobic and hydrophilic groups and having a carbohydrate content of about 4% and a protein content of about 96% by weight.

2. A method of protecting humans from infection by Neisseria gonorrhoeae microorganisms which comprises administering an amount of vaccine which is capable of eliciting a protective antibody response in the human to be protected, said vaccine containing a POMP antigen free of contaminants which are toxic to humans characterized by the ability to elicit a bactericidal response in humans, consisting essentially of subunits with molecular weights of from 34,000 to 39,000 Daltons, containing both hydrophobic and hydrophilic groups and having a carbohydrate content of about 4% and a protein content of about 96% by weight.

* * * * *